United States Patent [19]

Kita

[11] Patent Number: 5,182,259
[45] Date of Patent: Jan. 26, 1993

[54] INTRAOCULAR ANTICOAGULANT INCLUDING ANTITHROMBIN III AND METHOD OF ADMINISTRATION

[76] Inventor: Kiyoshi Kita, No. 4-4-7-502, Honmachi, Shibuyaku, Tokyo, Japan

[21] Appl. No.: 391,323

[22] Filed: Jul. 25, 1989

[30] Foreign Application Priority Data

Jul. 25, 1988 [JP] Japan .................................. 63-183680
Nov. 10, 1988 [JP] Japan .................................. 63-282398

[51] Int. Cl.$^5$ ..................... A61K 37/02; A61K 47/36; A61M 35/00
[52] U.S. Cl. ......................................... 514/8; 514/822; 514/912; 514/801; 514/54; 514/57; 604/289; 604/290
[58] Field of Search ................ 424/530; 604/289, 290; 514/801, 8, 822, 54, 57, 912; 530/393; 623/4-6

[56] References Cited

U.S. PATENT DOCUMENTS 4,340,589 7/1982 Uemura et al. .......................... 514/8
4,731,080 3/1988 Galin ....................................... 623/6

*Primary Examiner*—Jacqueline Stone
*Attorney, Agent, or Firm*—Staas & Halsey

[57] ABSTRACT

An intraocular anticoagulant including antithrombin III is applicable as an injection into the ocular chamber of the eye at the time of cataract surgery, intraocular lens implant surgery, and other ocular surgeries. The anticoagulant prevents fibrin deposits from forming on the intraocular lens surface after surgery and avoids postoperative viscoelastic material inducing transient elevation in intraocular pressure.

4 Claims, No Drawings

INTRAOCULAR ANTICOAGULANT INCLUDING ANTITHROMBIN III AND METHOD OF ADMINISTRATION

BACKGROUND OF THE INVENTION

The biophysical element, antithrombin, which inhibits thrombin action, theoretically exists in several types, such as, I, II, III, etc. However, only antithrombin III has been proved to actually exist. That is, it is synthesized in the human liver, exists in the human blood, and controls the coagulation system. It has also been proved that antithrombin III inhibits thrombin action more quickly in the presence of heparin. In other words, heparin itself does not cause anticoagulation, but it promotes the action of antithrombin III for immediate anticoagulation.

Antithrombin III is one of the major regulators of enzymes generated during the activation of the coagulation system. For this reason, antithrombin levels are expected to decrease in patients with a substantial activation of their coagulation system. This should occur when the rate of antithrombin III consumption exceeds its rate of production by the liver hepatocyte. This has been documented by a number of investigators who measured antithrombin III levels in clinical conditions that are associated with disseminated intravascular coagulation (D.I.C.) and several other conditions including malignancies, acute promyelocytic leukemias, severe burns with infections, sepsis and preeclampsia.

In order to provide proper treatment for D.I.C. in the past, heparin was mainly administered therewith. However, it has already been shown that heparin does not work effectively when antithrombin III is decreased in the blood. Accordingly, it has been recommended to administer dried concentrated human antithrombin III, so that the lack of antithrombin III can be corrected.

With regard to the effect of dried concentrated antithrombin III, no report has been issued, wherein the clinical use of antithrombin III in ophthalmology has been suggested.

More particularly, a patient's visual acuity is effected by fibrin deposits that form on an intraocular lens surface a few days after the intraocular lens has been implanted in a cataract patient.

To prevent fibrin accumulations, many surgeons have prescribed anti-inflammatory drugs such as Indomethacin or Corticosteriods. Unfortunately these drugs may produce significant harmful side effects.

Such fibrin deposits on the implanted intraocular lens surface is a problem which must be resolved because obstruction of the patient's vision or postoperative posterior synechia may result.

As previously mentioned, anti-inflammatory drugs are used to treat this condition, but the administration of Indomethacin or Corticosteroids is associated with a delay in wound healing according to reliable medical/clinical reports recently.

Fibrin formation in the ocular chamber is regarded as a formation occurring on the outside of blood vessels, and fibrin clot formation on the intraocular lens is regarded as iridocyclitis caused by fibrin deposition.

When the blood aqueous barrier is broke, the aqueous humor becomes similar to blood plasma and is confronted with corneal endothelial cells which look quite similar to blood endothelial cells, both in style and function. The ocular chamber, which is inherently not a blood vessel, becomes similar to a blood vessel for the time being.

On checking the movement of tissue plasminogen activator after cataract surgery or intraocular lens implant surgery, the degree to which the blood aqueous barrier breaks reaches the maximum after said surgery (after 1 or 2 days), and it recovers gradually after a period of time. However, the activation value of tissue plasminogen activator shows a two-phase deterioration, such that some deterioration is seen on the first day after the surgery, while rapid and conspicuous recovery is seen on the second day. This type of deterioration is evidence of the transient situation of the corneal endothelial cell function, and the recovery is evidence of the reaction of the cells' function against fibrinolytic action for coagulation in the aqueous humor.

Fibrin formation on an implanted intraocular lens, that occurs on the fourth to seventh postoperative days, is noticed with the activation of the intrinsic pathway of the blood coagulation system on the polymethylmethacrylate surface in the fibrinogen-rich aqueous humor. Consequently, the imbalance between coagulation and the fibrinolytic system in the aqueous humor may result in the fibrin formation on the implanted intraocular lens.

SUMMARY OF THE INVENTION

As discussed above, in the aqueous humor in the ocular chamber, the deterioration of anticoagulation and dissolving fibrin are unavoidable. In order to prevent such situations, this invention introduces antithrombin III into the aqueous humor to inhibit the action of thrombin as well as fibrin clot formations. The molecular weight of the antithrombin is preferably 59,000 to 65,000.

Antithrombin III is also mixed with sodium hyaluronate so that the effective time is kept as long as possible, wherein it can prevent coagulation and consumption of plasminogen activator derived from corneal endothelial cells.

Therefore, this anticoagulant has been invented for use in intraocular surgery such as cataract and vitreous operations. In the ocular chamber of the eye, where this anticoagulant is injected, antithrombin III is considered to inhibit the accelerated activity of thrombin and prevent fibrin clot formation.

The viscoelastic solution of sodium hyaluronate has been used in many cases of cataract and intraocular lens implant surgery. Its molecular weight generally ranges from 0.7 million to 10 million.

This solution is indispensable for ocular surgery, since it prevents damage to corneal endothelial cells and protects the ocular organization and so on.

The solution is usually removed just before the completion of surgery. There is, however, evidence that some sodium hyaluronate remains and causes elevation of intraocular pressure due to inflammation, where some pressure reducing substances must be used as a treatment.

This invention has the object of using as an anticoagulant an injection solution of antithrombin III and sodium hyaluronate.

This invention also has as a purpose the use of antithrombin III in therapeutic ophthalmology.

This invention aims to prevent fibrin clot formation on the intraocular lens surface by injecting antithrombin III anticoagulant into the ocular chamber during cataract and intraocular lens implant surgery.

In order to prevent fibrin clot formation, sodium hyaluronate is mixed with antithrombin III to establish a viscoelastic anticoagulant.

When the cataract and intraocular lens implant surgery is finished, the ocular chamber is washed and filled with physiological sodium chloride solution and the incisions are sutured.

This invention aims to prevent fibrin clot formation which might cause elevation of intraocular pressure when sodium hyaluronate is used as a viscoelastic material in ocular surgery.

DETAILED DESCRIPTION OF THE PREFERRED EMBODIMENTS

When cataract and intraocular lens implant surgery is finished, the ocular chamber is washed and filled with physiological sodium chloride solution and the incisions are sutured.

The blood aqueous barrier is broken by the intraocular surgery, with the inflow of plasminogen activator inhibitor from the blood and the decreased activity of plasminogen activator released from the corneal endothelial cells. This creates an imbalance of the coagulation and the fibrinolytic systems in the fibrinogen-rich aqueous humor, resulting in the conversion of fibrinoger to fibrin.

For the purpose of improved treatment, this invention provides antithrombin III in a viscoelastic solution for therapeutic use.

Antithrombin III gradually inhibits the action of thrombin, when heparin is absent, and instantaneously neutralizes thrombin when heparin is present.

Sodium hyaluronate, a large polysaccharide molecule, is present in nearly all connective tissue matrices of vertebrate organisms. In the human body, it is an important structural element in the skin, sutcutaneous and interstitial connective tissues, synovial tissue and fluid, umbilical cord and the vitreous. In the eye, sodium hyaluronate can be found not only in the vitreous but also in the aqueous humor and in the connective tissues of the gonio angle. It has been confirmed that sodium hyaluronate solution is safe for corneal implant surgery and intraocular lens implant surgery.

In the case of cataract and intraocular lens implant surgery, this viscoelastic solution has been used in the ocular chamber, and has been taken out immediately after the surgery was finished. However, the solution tends to remain in the ocular chamber because of its viscoelastic nature.

It has been reported that sodium hyaluronate of a molecular weight of approximately 2.2 million, which is generally used as a viscoelastic material, tends to remain normally in the ocular chamber for 3 days. However, there is another report that it takes 6 days for the solution to dissipate. In the case where intraocular lens designed for nd-yag laser treatment is used it takes even longer for the solution to dissipate.

In view of the fact that the viscoelastic solution needs from 3 to 6 days to dissipate, this invention describes a mixture of antithrombin III with a viscoelastic solution, whereas the antithrombir III works slowly and gradually in the most effective way to control the fibrin accumulation on the intraocular lens surface.

As the viscoelastic material, sodium hyaluronate solution, natural methylcellulose solution or collagen solution are preferred.

The preferred embodiment of the method invention includes mixing, as an anticoagulant, antithrombin III with sodium hyaluronate of high molecular weight, dissolving same in distilled water with buffering agents, such as sodium chloride, sodium phosphate, crystalline dissodium phosphate, sodium citrate or aminoacetic acid, and using this final solution by injection as an ocular anticoagulant.

Even if the vitreous body is involved in the surgery, the treatment by this invention results in the vitreous cavity being protected against fibrin accumulations.

The fibrin formation on an implanted intraocular lens, that occurs on the fourth to seventh postoperative day, is still one of the most serious postoperative complications.

The pathogenesis of the fibrin formation on the implanted intraocular lens has been obscured so far.

Recently, it is noticed that the activation of the intrinsic pathway of the blood coagulation system on the polymethylmethacrylate surface in the fibrinogen-rich aqueous humor and decreased activity of tissue plasminogen activator released from the corneal endothelial cells, are probably due to the surgical trauma. Consequently, it is speculated that the imbalance between coagulation and the fibrinolytic system in the aqueous humor results in the fibrin formation on the intraocular lens.

Antithrombin III is a glycoprotein of about 59,000 to 65,000 in molecular weight. It forms a complex with heparin and shows strong anti-thrombin effect. This invention is preferably directed to local administration of antithrombin III into the human ocular chamber and vitreous cavity in order to improve the intracameral hypercoagulability.

The magnified value of antithrombin III mentioned hereunder in the Examples is dependent upon the figure of a normal person who has in theory 1 time value of antithrombin III in 1 ml of blood.

Without further elaboration, it is believed that one skilled in the art, using the preceding description, can utilize the present invention to its fullest extent. The following preferred specific Examples are, therefore, to be construed as merely illustrative, and not limitative in any way whatsoever, of the remainder of the disclosure.

EXAMPLE I

Ten white rabbits were used. Five were given an antithrombin III injection and the others were given a physiological saline injection, into their ocular chambers, respectively.

The antithrombin III used in this experiment was the anticoagulant ANTHROBIN sold by HOECHST JAPAN LIMITED which has an activity 50 times greater than antithrombin found in normal human blood.

After nembutal anesthesia, an incision of 3 mm in width was made at 12 o'clock of the corneo-scleral border with a razor blade The aqueous humor was aspirated with a 27 gauge disposable needle and 0.05 to 0.1 ml of the antithrombin III solution or the physiological saline was injected into the chamber at 3 o'clock of the corneo-scleral border.

Two and five hours after the experiment, rabbits were sacrificed.

The enucleated eye balls were fixed with glutaraldehyde, and the iris and the trabecular tissue were separated for scanning electron microscopic and transmission electron microscopic examination.

In the physiological saline injection group, the scanning electron microscopic examination revealed fibrinous and reticular tissue on the iris surface, where round inflammatory cells were associated. The transmission electron microscopic examination revealed fibrin nets and macrophages on iris hyperplastic fibroblasts and in the intertrabecular spaces.

On the other hand, in the antithrombin III injection group, the scanning electron microscopic and the transmission electron microscopic examinations revealed no fibrin deposition on the iris surface nor in the trabecular tissue.

In accordance with the above results, the antithrombin III solution of high activity is considered to inhibit fibrin deposition on the iris and in the trabecular tissue, under the condition of mild fibrinous iridocyclitis in the rabbits. In addition, no hyphema was observed.

Through this experiment, antithrombin III was considered to be safely and effectively administered in the human eye.

EXAMPLE II

Antithrombin III of a molecular weight of approximately 59,000 to 65,000 was dissolved in 1 ml physiological sodium chloride solution to obtain a concentration of 50 folds value per ml, whereafter the solution was mixed with buffering agents of 3 mg sodium citrate and 9 mg aminoacetic acid and finally it was used as an injection. No heparin was used.

EXAMPLE III

Sodium hyaluronate of a molecular weight of approximately 1 million to 4 million, and antithrombin III of a molecular weight of approximately 59,000 to 65,000, were dissolved into 1 ml physiological sodium chloride solution to obtain 50 folds value per ml, whereafter it was mixed with buffering agents of 0.25 mg sodium phosphate, 0.04 mg crystalline dissodium phosphate, 3 mg sodium citrate and 9 mg aminoacetic acid, and finally it was used as an injection.

The preceding Examples can be repeated with similar success by substituting the generically or specifically described reactants and/or operating conditions of this invention for those used in the preceding Examples.

By introducing this new intraocular anticoagulant containing antithrombin III into the eye of the cataract patient at the time of surgery, fibrin clot formation on the implanted intraocular lens can be prevented. Moreover, antithrombin III decreases the complications that have been associated with conventional excessive use of Indomethacin or Corticosteriods.

Further, by introducing this novel viscoelastic material containing antithrombin III to the ocular chamber of the cataract patient at surgery, fibrin clot formation and viscoelastic material-inducing high elevation in intraocular pressure are both prevented. In this regard, the invention decreases the complications seen with the excessive use of pressure-decreasing and anti-inflammatory drugs such as Acetazolamide, Timolol, Indomethacin and Corticosteroids.

As explained above, this invention prevents transient situational elevation of intraocular pressure, prevents the transient deterioration of visual acuity and eye pain, and provides an anticoagulant which is safely applicable as a viscoelastic material for ophthalmological treatments.

The foregoing is considered illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to that fall within the scope of the invention and the appended claims.

I claim:

1. A method of preventing fibrin clot formation and viscoelastic material-inducing elevation in intraocular pressure in a patient in need thereof, comprising the steps of:

forming a solution including antithrombin III in an amount effective to present the viscoelastic material-induced elevation in intraocular pressure and a viscoelastic material; and administering the solution into the ocular chamber during eye surgery.

2. A method of preventing fibrin clot formation and viscoelastic material-inducing elevation in intraocular pressure in a patient in need thereof, comprising the steps of:

forming a solution including antithrombin III in an amount effective to present the viscoelastic material-induced elevation in intraocular pressure and a viscoelastic material; and administering the solution during eye surgery wherein the administering step comprises the step of: administering the solution to the vitreous cavity.

3. The method as recited in claim 1, further comprising the step of selecting the viscoelastic material from a sodium hyaluronate solution, natural methylcellulose solution and collagen solution.

4. The method as recited in claim 2, further comprising the step of selecting the viscoelastic material from a sodium hyaluronate solution, natural methylcellulose solution and collagen solution.

* * * * *

UNITED STATES PATENT AND TRADEMARK OFFICE
CERTIFICATE OF CORRECTION

PATENT NO. : 5,182,259
DATED       : January 26, 1993
INVENTOR(S) : KIYOSHI KITA It is certified that error appears in the above-identified patent and that said Letters Patent is hereby corrected as shown below:

Col. 3, line 36, "sutcutaneous" should be --subcutaneous--;

Col. 3, line 61, "antithrombir" should be --antithrombin--;

Col. 6, line 27, "present" should be --prevent--;

Col. 6, line 37, "present" should be --prevent--.

Signed and Sealed this

Thirtieth Day of November, 1993

Attest:

BRUCE LEHMAN

Attesting Officer

Commissioner of Patents and Trademarks